US00PP14251P29

(12) United States Plant Patent
van den Bosch

(10) Patent No.: US PP14,251 P2
(45) Date of Patent: Oct. 28, 2003

(54) HYPERICUM PLANT NAMED 'BOSASUGA'

(50) Latin Name: *Hypericum androsaemum*
Varietal Denomination: Bosasuga

(75) Inventor: Bernard Renee van den Bosch, Rijinsburg (NL)

(73) Assignee: H. & B. R. Van den Bosch, Rijnsburg (NL)

( * ) Notice: Subject to any disclaimer, the term of this patent is extended or adjusted under 35 U.S.C. 154(b) by 0 days.

(21) Appl. No.: 10/228,458

(22) Filed: Aug. 27, 2002

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Hypericum plant named 'Bosasuga', characterized by its upright and outwardly spreading plant habit; dark green-colored leaves; shiny light red-colored fruits; and good postproduction longevity.

4 Drawing Sheets

Botanical classification/cultivar designation: *Hypericum androsaemum* cultivar Bosasuga.

BACKGROUND OF THE INVENTION

The present Invention relates to a new and distinct cultivar of Hypericum plant, botanically known as *Hypericum androsaemum,* commercially used as cut stems with fruits, and hereinafter referred to by the name 'Bosasuga'.

The new Hypericum is a product of a planned breeding program conducted by the Inventor in Rijnsburg, The Netherlands. The objective of the breeding program was to develop cut Hypericum varieties with attractive fruit coloration.

The new cultivar originated from a cross-pollination made by the Inventor in July, 1993 of a proprietary selection of *Hypericum androsaemum* identified as code number 93, not patented, as the female, or seed, parent with a proprietary selection of *Hypericum androsaemum* identified as code number 28, not patented, as the male, or pollen, parent. The cultivar Bosasuga was discovered and selected by the Inventor in July, 1995 as a flowering plant within the progeny of the stated cross-pollination in a controlled environment in Rijnsburg, The Netherlands.

Asexual reproduction of the new Hypericum by terminal cuttings taken at Rijnsburg, The Netherlands since March, 1996, has shown that the unique features of this new Hypericum are stable and reproduced true to type in successive generations of asexual reproduction.

SUMMARY OF THE INVENTION

The following traits have been repeatedly observed and are determined to be the unique characteristics of 'Bosasuga'. These characteristics in combination distinguish 'Bosasuga' as a new and distinct cultivar:

1. Upright and outwardly spreading plant habit.
2. Dark green-colored leaves.
3. Shiny light red-colored fruits.
4. Good postproduction longevity.

Plants of the new Hypericum differ from plants of the parent selections primarily in fruit coloration.

Plants of the new Hypericum can be compared to plants of the Hypericum cultivar Bosapin, disclosed in U.S. Plant Pat. No. 10,993. In side-by-side comparisons conducted in Rijnsburg, The Netherlands, plants of the new Hypericum differed from plants of the cultivar Bosapin in the following characteristics:

1. Plants of the new Hypericum had smaller leaves than plants of the cultivar Bosapin.
2. Plants of the new Hypericum had smaller fruits than plants of the cultivar Bosapin.
3. Plants of the new Hypericum had lighter red-colored fruits than plants of the cultivar Bosapin.

Plants of the new Hypericum can also be compared to plants of the Hypericum cultivar Bosakin, disclosed in U.S. Plant Pat. No. 10,994. In side-by-side comparisons conducted in Rijnsburg, The Netherlands, plants of the new Hypericum differed from plants of the cultivar Bosakin in the following characteristics:

1. Plants of the new Hypericum were shorter than plants of the cultivar Bosakin.
2. Plants of the new Hypericum had smaller leaves than plants of the cultivar Bosakin.
3. Plants of the new Hypericum had smaller fruits than plants of the cultivar Bosakin.
4. Plants of the new Hypericum had light red-colored fruits whereas plants of the cultivar Bosakin had dark red-colored fruits.

BRIEF DESCRIPTION OF THE PHOTOGRAPHS

The accompanying colored photographs illustrate the overall appearance of the new Hypericum, showing the colors as true as it is reasonably possible to obtain in colored reproductions of this type. Colors in the photographs may differ slightly from the color values cited in the detailed botanical description which accurately describe the colors of the new Hypericum.

The photograph on the first sheet comprises a side perspective view of typical plants of 'Bosasuga' with flowers and fruits.

The photograph on the second sheet is a close-up view of a typical plant of 'Bosasuga'.

The photographs on the third and fourth sheets are close-up views of typical leaves, flowers and fruits of 'Bosasuga'.

DETAILED BOTANICAL DESCRIPTION

The new Hypericum has not been observed under all possible environmental conditions. The phenotype may vary somewhat with variations in environment such as temperature, daylength and light intensity, without, however, any variance in genotype.

The aforementioned photographs, following observations and measurements describe plants grown in Rijnsburg, The Netherlands, in an outdoor nursery and under commercial production practices. Plants were about two years old. The photographs and description were taken in September when outdoor day temperatures ranged from 14 to 27° C. and day temperatures ranged from 5 to 14° C. In the following description, color references are made to The Royal Horticultural Society Colour Chart, 2001 Edition, except where general terms of ordinary dictionary significance are used.

Botanical classification: *Hypericum androsaemum* cultivar Bosasuga.

Parentage:

*Female parent.*—Proprietary selection of *Hypericum androsaemum* identified as code number 93, not patented.

*Male parent.*—Proprietary selection of *Hypericum androsaemum* identified as code number 28, not patented.

Propagation:

*Type.*—Terminal cuttings.

*Time to initiate roots.*—Summer: About 14 days at 20° C. Winter: About 21 days at 15° C.

*Time to produce a rooted cutting.*—Summer: About two months at 20° C. Winter: About three months at 15° C.

*Root description.*—Fine; white in color.

*Rooting habit.*—Freely branching, dense.

Plant description:

*Plant form.*—Upright and outwardly spreading perennial woody shrub; globular to broadly globular in shape.

*Growth habit.*—Moderately vigorous. Freely basal branching; dense and bushy growth habit.

*Plant height.*—About 65 cm.

*Plant width (spread).*—About 70 cm.

*Quantity of stems per year.*—About nine.

*Lateral branches.*—Length: About 11 cm. Diameter: About 2 mm. Internode length: About 2.9 cm. Strength: Moderate. Texture: Smooth; glabrous. Color: 144B overlain with 183B.

*Foliage description.*—Leaves opposite; single; sessile and generally symmetrical. Length: About 6.2 cm. Width: About 4.1 cm. Shape: Broadly ovate. Apex: Obtuse. Base: Obtuse with cordate tendencies. Margin: Entire. Texture: Glabrous; slightly rugose. Venation pattern: Pinnate. Color: Developing leaves, upper surface: Between 141A and 143A. Developing leaves, lower surface: 138B. Fully expanded leaves, upper surface: 137A. Fully expanded leaves, lower surface: 138B. Venation, upper surface: 144C to 144D. Venation, lower surface: 144C.

Flower description:

*Flower type and habit.*—Bright yellow single flowers arranged in terminal compound umbels with about 12 flowers per lateral branch. Flowers not fragrant. Flowers not persistent. Flowers upright.

*Natural flowering season.*—Summer, typically July through early September in Rijnsburg, The Netherlands; flowering period typically lasts about 60 days.

*Postproduction longevity.*—Cut stems are typically harvested when all flowers have developed fruits. Postproduction longevity of cut stems with fruits is about two weeks.

*Inflorescence height.*—About 6.5 cm.

*Inflorescence diameter.*—About 7 cm.

*Flower buds.*—Height: About 7 mm. Diameter: About 7 mm. Shape: Ovoid. Color: Apex and mid-section, 17A to 17B; towards base, 5A to 5B.

*Flowers.*—Diameter: About 3.1 cm. Depth: About 1.9 cm.

*Petals.*—Quantity per flower: Five. Length: About 1.4 cm. Width: About 1 cm. Shape: Broadly elliptic. Aspect: Concave. Apex: Shallowly retuse to emarginate. Base: Attenuate. Margin: Entire. Texture, upper and lower surfaces: Smooth. Color: Developing and fully expanded petals, upper surface: 14A to 14B; color does not fade with subsequent development. Developing and fully expanded petals, lower surface: 14A to 14B.

*Sepals.*—Quantity per flower: Five. Length: About 1.3 cm. Width: About 8 mm. Shape: Broadly elliptic. Apex: Obtuse to abruptly acute. Base: Broadly cuneate. Margin: Entire. Aspect: Slightly reflexed. Texture, upper and lower surfaces: Smooth. Color: Developing and fully expanded sepals, upper surface: 143A. Developing and fully expanded sepals, lower surface: 137D.

*Peduncles.*—Length: About 2.8 cm. Diameter: About 1.5 mm. Orientation: Erect to about 45° from vertical. Strength: Moderately strong. Color: 144A to 144B.

*Pedicels.*—Length: About 1.1 cm. Diameter: About 1 mm. Orientation: Erect to about 45° from vertical. Strength: Moderately strong. Color: 144B.

*Reproductive organs.*—Stamens: Quantity per flower: About 85. Anther shape: Broadly ovate. Anther length: About 0.75 mm. Anther color: 17A to 17B. Pollen amount: Moderate. Pollen color: 13A. Pistils: Quantity per flower: Three. Pistil length: About 5 mm. Stigma shape: Globular. Stigma color: Close to 45A. Style length: About 5 mm. Style color: 154B. Ovary color: 150B to 154B.

*Fruits.*—Quantity per flower: One. Days to ripening: About 25. Longevity on the plant: About 30 days. Type: Capsule. Shape: Ellipsoidal. Length: About 1.2 cm. Diameter: About 1 cm. Texture: Smooth, glabrous. Color: 47B to 50A.

*Seeds.*—Quantity per fruit: More than 100. Length: About 0.8 mm. Diameter: About 0.5 mm. Texture: Smooth, glabrous. Color: N199C to slightly darker than N199C.

Disease/pest resistance: Plants of the new Hypericum have not been observed to be resistant to pathogens and pests common to Hypericum.

Temperature tolerance: Plants of the new Hypericum have been observed to tolerate temperatures ranging from −15 to 35° C.

It is claimed:

1. A new and distinct cultivar of Hypericum plant named 'Bosasuga', as illustrated and described.

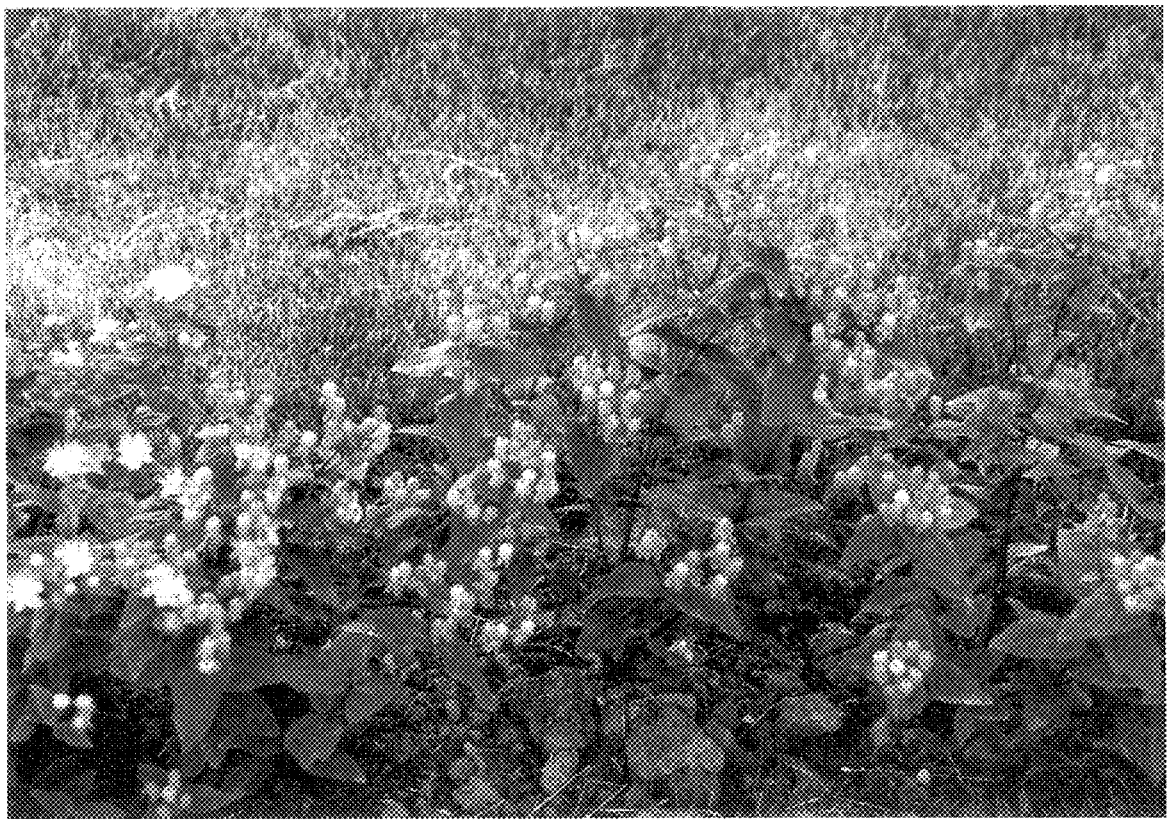

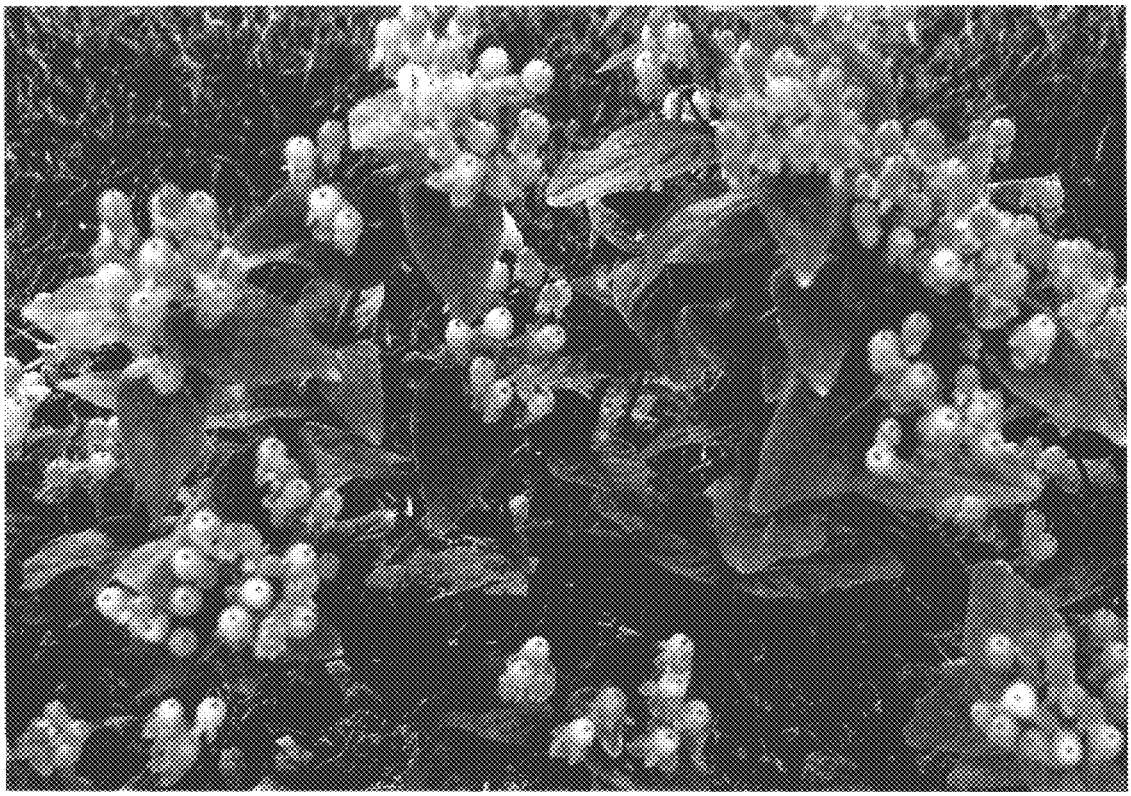

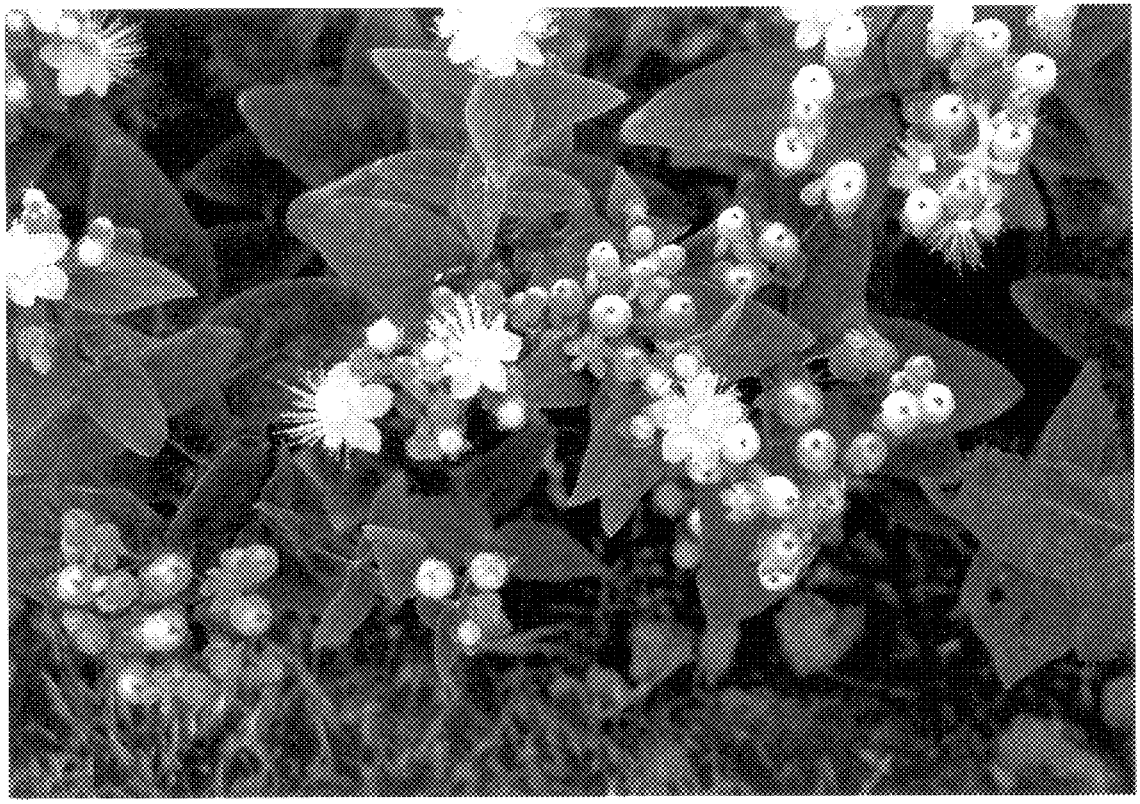

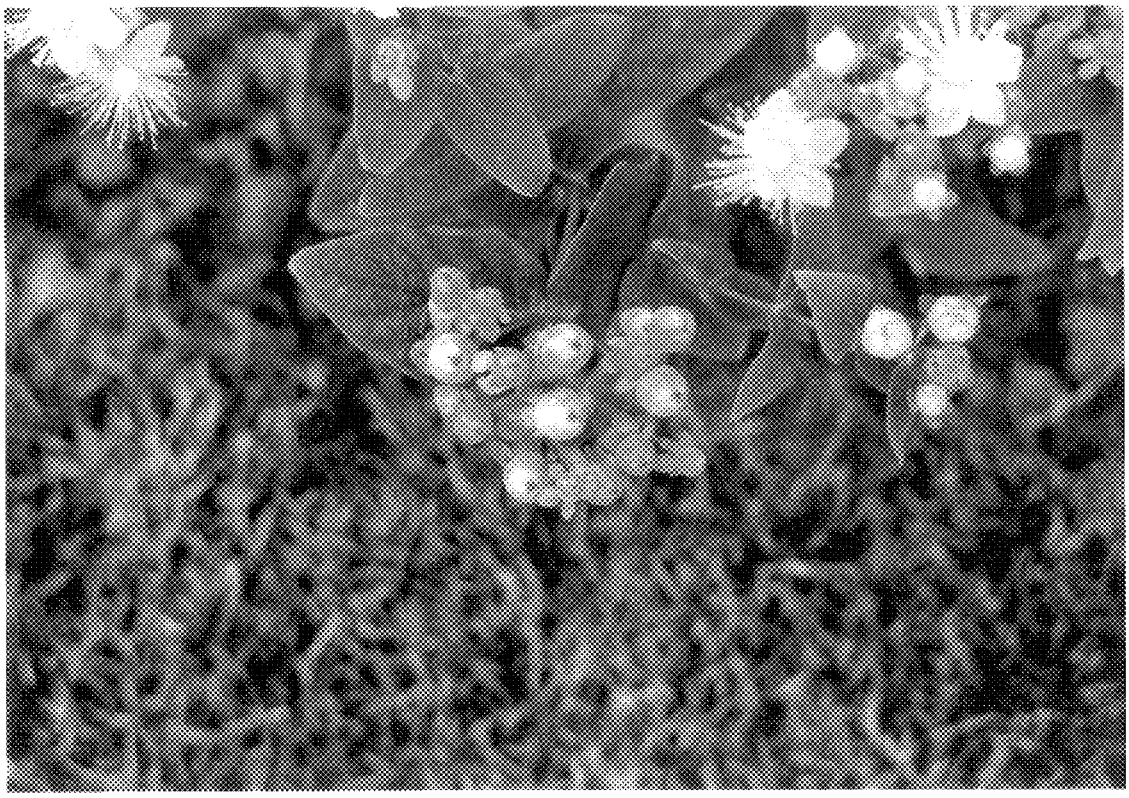

* * * * *